(12) United States Patent
Spanholtz

(10) Patent No.: US 9,193,953 B2
(45) Date of Patent: Nov. 24, 2015

(54) METHODS AND MEANS FOR STEM CELL PROLIFERATION AND SUBSEQUENT GENERATION AND EXPANSION OF PROGENITOR CELLS

(75) Inventor: Jan Spanholtz, Kleve (DE)

(73) Assignee: IPD-THERAPEUTICS B.V., Bilthoven (NL)

( * ) Notice: Subject to any disclaimer, the term of this patent is extended or adjusted under 35 U.S.C. 154(b) by 921 days.

(21) Appl. No.: 12/593,128

(22) PCT Filed: Mar. 27, 2008

(86) PCT No.: PCT/NL2008/050174
§ 371 (c)(1),
(2), (4) Date: Mar. 19, 2010

(87) PCT Pub. No.: WO2008/118020
PCT Pub. Date: Oct. 2, 2008

(65) Prior Publication Data
US 2010/0178275 A1 Jul. 15, 2010

(30) Foreign Application Priority Data
Mar. 27, 2007 (EP) .................................. 07105060

(51) Int. Cl.
*C12N 5/00* (2006.01)
*C12N 5/0789* (2010.01)
*C12N 5/0783* (2010.01)

(52) U.S. Cl.
CPC ............ *C12N 5/0647* (2013.01); *C12N 5/0646* (2013.01); *C12N 2500/12* (2013.01); *C12N 2501/125* (2013.01); *C12N 2501/145* (2013.01); *C12N 2501/21* (2013.01); *C12N 2501/22* (2013.01); *C12N 2501/2302* (2013.01); *C12N 2501/235* (2013.01); *C12N 2501/2306* (2013.01); *C12N 2501/2307* (2013.01); *C12N 2501/2315* (2013.01); *C12N 2501/26* (2013.01); *C12N 2501/90* (2013.01)

(58) Field of Classification Search
None
See application file for complete search history.

(56) References Cited

U.S. PATENT DOCUMENTS 5,087,570 A * 2/1992 Weissman et al. ........... 424/93.7

FOREIGN PATENT DOCUMENTS

| WO | 9949881 A2 | 10/1999 |
| WO | 2005095584 A1 | 10/2005 |
| WO | 2005105982 A1 | 11/2005 |
| WO | 2007037682 A1 | 4/2007 |

OTHER PUBLICATIONS

Muench et al., "Differential effects of interleukin-3, interleukin-7, interleukin 15, and granulocyte-macrophage colony-stimulating factor in the generation of natural killer and B cells from primitive human fetal liver progenitors," Experimental Hematology, 28:961-973 (2000).
Carayol et al., "NK cells differentiated from bone marrow, cord blood and peripheral blood stem cells exhibit similar phenotype and functions," Eur. J. Immunol., 28:1991-2002 (1998).
Yu et al., "Flt3 Ligand Promotes the Generation of a Distinct CD34+ Human Natural Killer Cell Progenitor That Responds to Interleukin-15," Blood, 92(10):3647-3657 (1988).
Schubert, Mario, "Einfluss regioselektiv modifizierter Heparansulfate auf den Erhalt und die Expansion primitiver hamatopoetischer Stammzellen und Vorlauferzellen," <<http://www.doktor-schubert.de/downloads/Dissertation%20M.Schubert.pdf>>, retrieved Jan. 1, 2004.
Gupta et al., "Human LTC-IC can be maintained for at least 5 weeks in vitro when interleukin-3 and a single chemokine are combined with O-sulfated heparan sulfates: Requirement for optimal binding interactions of heparan sulfate with early-acting cytokines and matrix proteins," Blood, 95(1):147-155 (2000).

* cited by examiner

*Primary Examiner* — Blaine Lankford
(74) *Attorney, Agent, or Firm* — Hoffmann & Baron, LLP

(57) ABSTRACT

The invention is related to methods for expanding and differentiating hemopoietic progenitor cells in a medium comprising a collection of cytokines, desulphated glycosaminoglycan and human serum. The invention further relates to a collection of cells obtainable by a method of the invention, use of the collection of cells, and a kit of parts for expanding and differentiating hemopoietic progenitor cells.

14 Claims, 3 Drawing Sheets

METHODS AND MEANS FOR STEM CELL PROLIFERATION AND SUBSEQUENT GENERATION AND EXPANSION OF PROGENITOR CELLS

This application is the U.S. National Phase of, and Application claims priority from, International Application Number PCT/NL2008/050174filed 27 Mar. 2008 and European Patent Application No. 07105060.3 filed 27 Mar. 2007, each of which are incorporated herein by reference

BACKGROUND OF THE INVENTION

The invention relates to the field of modern medical biology. In particular the invention relates to stem cell technology. More in particular the invention relates to stem cell technology, in particular postembryonic stem cell technology.

Stem cells are primal undifferentiated cells which have the ability for self-renewal and the ability to differentiate into other cell types. This ability allows them to act as a repair system for the body, replenishing other cells as long as the organism is alive.

Stem cells are categorized by potency which describes the specificity of that cell.

Totipotent stem cells are cells that have the ability of self renewal and are capable of differentiating into any and all cell type to form an entire new organism. They are typically produced from the fusion of an egg and sperm cell. Cells produced by the first few divisions of the fertilized egg cell are also totipotent. These cells can grow into any cell type without exception.

Pluripotent stem cells are the descendants of totipotent cells and can grow into any cell type except for totipotent stem cells.

Multipotent stem cells can produce only cells of a closely related family of cells (e.g. hematopoietic stem cells can differentiate into blood cells such as red blood cells, white blood cells and platelets).

Unipotent cells (sometimes called progenitor cells) can produce only one cell type; but, have the property of self-renewal which distinguishes them from non-stem cells.

Stem cells are also categorized according to their source, as either adult (postembryonic) or embryonic stem cells.

Adult stem cells are undifferentiated cells found among differentiated cells of a specific tissue and are mostly multipotent cells. They are more accurately called somatic stem cells, because they need not come from adults but can also come from children or umbilical cords.

Embryonic stem cells are cells obtained from the undifferentiated inner mass cells of a blastocyst, an early stage embryo that is 50 to 150 cells.

Blood from the placenta and umbilical cord that are left over after birth is one source of adult stem cells. It is collected by removing the umbilical cord, cleansing it and withdrawing blood from the umbilical vein. Other sources are bone marrow (BM) or G-CSF-mobilized peripheral blood (mPB)

Red blood cells and platelets can be removed from the cord blood, BM or in PB and the remaining cells containing the stem cells can be used or stored (e.g. in liquid nitrogen).

Stem cells themselves are useful in many applications of so-called regenerative medicine. They have been used to treat heart disease, repair spinal cords and many other diseases where tissues of all kinds needed to be replaced.

Stem cells can also be used to produce certain kinds of differentiated cells that are effector cells in certain diseases.

Unfortunately however, stem cells are present in the body of a mammal in small quantities only. Often they are present in organs or tissues that can not easily be reached. Embryonic stem cell are also not easily obtainable and only in minute quantities. Moreover, there are some ethical concerns in growing embryos merely for the purpose of producing stem cells. There is a need therefore for methods for multiplying available stem cells and/or primitive lineage specific progeny thereof, without differentiating into less potent descendants. Totipotent stem cells should remain totipotent after expansion and not turn into pluripotent stem cells, pluripotent stem cells should remain pluripotent, etc. In some instances the change into a less potent descendant may be acceptable (at least to a certain extent) as long as the potential for self renewal and at least multipotency is retained.

THE SUMMARY OF THE INVENTION

Although stem cells have the ability of self-renewal, expanding and/or maintaining stem cells in culture is not an easy task. In its broadest sense the present invention provides a technology for stem cell culture and/or expansion and/or differentiation comprising a number of elements that are extremely suitable for just that purpose.

Thus, in one embodiment the invention provides a medium for culturing, expanding and/or subsequently differentiating stem cells into specifically desired target-effector cells, said medium comprising a basic cell culture medium, 0-25% human serum, 0.1-100 mg/l desulphated Glycosaminoglycan (GAG), preferably heparin (=UFH) or a functional equivalent thereof. Preferably said GAG/UHF is completely desulphated. Preferably said GAG/UHF is unfractionated. In a particularly preferred embodiment said GAG is low molecular weight GAG (LMWH). In a particularly preferred embodiment said low molecular weight GAG is a low molecular weight heparin, preferably derived from standard heparin by UFH-depolymerization. Low molecular weight heparins (LMWHs), consist of short chains of polysaccharide. LMWHs are defined as heparin or heparin salts having an average molecular weight of between about 2000-10000 dalton, preferably between 5000 and 8000 dalton and more preferably about 8000 dalton, with preferably at least 60% of the chains being less then the average chain length. When the low molecular weight heparin average about 8000 dalton it is preferred that at least 60% of all chains have a molecular weight less than 8000 Da. LMWHs can be obtained by various methods of fractionation or depolymerisation of polymeric heparin.

Various methods of heparin depolymerisation are used in the manufacture of low molecular weight heparin. A non-limiting list is given herein below. A heparin of the invention can obtained from a mammal or other organism such as snails, alternatively heparines are synthesized synthetically or semi-synthetically. An example of the latter is production of heparin in bacteria such as but not limited to the heparin K5 by *E. coli*. Modifications of heparine such but not limited to acytylation, desulphatation phosphorylation are also considered to be a heparin as defined in this invention. Non-limiting but preferred examples of such modifications are LMWH completely or partially desulfated, LMWH completely or partially desulfated and completely or partially Re—N-acetylated, LMWH completely or partially desulfated and completely or partially Re—N-sulfated, Substance L4: LMWH completely or partially desulfated and completely or partially Re—N-phosphorylated, less than 8000 Da and for which at least 60% of all chains have a molecular weight less than 8000 Da. These can be obtained by various methods of fractionation or depolymerisation of polymeric heparin. Various methods of heparin depolymerisation are used in the manufacture of low molecular weight heparin. A non-limiting list is given herein below.

Oxidative depolymerisation with hydrogen peroxide. Used in the manufacture of ardeparin (Normiflo®)

Deaminative cleavage with isoamyl nitrite. Used in the manufacture of certoparin (Sandoparine®)

Alkaline beta-eliminative cleavage of the benzyl ester of heparin. Used in the manufacture of enoxaparin (Lovenox® and Clexane®)

Oxidative depolymerisation with Cu2+ and hydrogen peroxide. Used in the manufacture of parnaparin (Fluxum®)

Beta-eliminative cleavage by the heparinase enzyme. Used in the manufacture of tinzaparin (Innohep® and Logiparin®)

Deaminative cleavage with nitrous acid. Used in the manufacture of dalteparin (Fragmin®), reviparin (Clivarin®) and nadroparin (Fraxiparin®)

A combination of suitable cytokines, preferably encompassing three or more of thrombopoietin, flt-3 ligand, stem cell factor, IL-3, IL-7, IL-15, IL-2 in saturating amounts (>4 ng/ml) as well as a combination of G-CSF, GM-CSF, IL-6, MIP-I-α, and LIF in physiological amounts (<250 pg/ml) and further conventional supplements, such as L-glutamine, antibiotics, ascorbic acid, selenium selenite, lithium salt, ethanolamine and 2-beta-mercaptoethanol. The cytokines given are chosen for their functions. For some of the cytokines given there are other cytokines which will at least in part be able to perform the same function. Those can then of course substitute the listed ones.

Preferably a medium according to the invention comprises about 1-100, more preferably about 15-50 mg/l of desulphated GAG/UFH or a functional equivalent thereof may be present in different amounts which are equivalent in activity to the amounts given for desulphated-UFH. Preferably 1-100 mg, more preferably 15-50 mg low molecular weight heparin (LMWH) is used, preferably derived from standard heparin by UFH-depolymerization. A functional equivalent may be present in different amounts which are equivalent in activity to the amounts given for LMWH.

The amounts of cytokine added are conventional in he art, preferred amounts are given in the examples, but 10% deviations in amount are very well acceptable and within the scope of the present invention.

Many basic media are known. A selection is given below, but many more may be suitable. Basic media include but are not limited to BEM (Basic Eagle Medium), DMEM (Dulbecco's modified Eagle Medium), Glasgow minimal essential medium, M199 basal medium, HAMs F-10, HAMs F-12, Iscove's DMEM, RPMI, Leibovitz L15, MCDB, McCoy 5A, StemSpan H3000® and StemSpanSFEM®, Stemline I™ and Stemline II™; X-Vivo10™, X-Vivo15™ and X-Vivo20™ etc.

Combinations of these basic media can also be used. Preferably serum-free formulations, such as Stemline I™ and Stemline II™, StemSpan H3000®, StemSpan SFEM® or X-Vivo10™, X-Vivo15™ and X-Vivo20™ will be used at the time point of initiation of culture with and/or without the addition of human serum. Combinations of DMEM and HAMs F-12 are preferred at specific time points according to the invention. The amounts given herein are typically suitable for cultures which are started with preferably with about 100,000 cells per ml. The amounts may be adapted for different amounts of cells with which cultures are started.

The media according to the invention can be varied in their serum content, preferably together with a different combination of cytokines to provide either an expansion medium or a differentiation medium and or alternatively an expansion+differentiation medium at defined time points according to the invention.

Thus, in one embodiment of the present invention a medium and a method for proliferating stem cells with subsequent generation of primitive lineage specified progenitor cells, particularly stem cells from umbilical cord blood (UCB), bone marrow (BM) or G-CSF-mobilized peripheral blood (mPB) is provided in a form that stem cell proliferation produces one daughter stem cell and one primitive progenitor stem cell, the latter with the ability of extensive self-renewal and functional maturation. Typically from 100,000 cells of a stem cell enriched population $>2\times10^6$ primitive progenitors can be generated while maintaining the stem cell pool. Each primitive progenitor is capable to produce $>1\times10^3$ functional maturated effector cells. The stem cell enriched population may be isolated CD34+ cells and/or CD133+ cells. Alternatively, mononuclear cells (MNC) that contain all CD34+ as well as all CD133+ cells are also suitable.

The present invention in said embodiment provides a medium for expanding stem cells comprising a basic cell culture medium, 1-100 mg/l desulphated-UFH and/or LMWH and/or derivatives thereof and a combination of suitable cytokines, preferably encompassing three or more of thrombopoietin, flt-3 ligand, stem cell factor, IL-3, IL-7, IL-15, in conventional (saturated amounts >4 ng/ml) as well as G-CSF, GM-CSF, IL-6, MIP-I-α, and LIF in physiological amounts (<250 pg/ml), and further conventional supplements, such as L-glutamine, antibiotics, ascorbic acid, selenium selenite, ethanolamine, lithium salt and 2-beta-mercaptoethanol.

Preferably, a medium for expansion according to the invention comprises 15-50 mg/l desulphated-UFH or LMWH. The preferred basic medium is a commercially available serum-free formulation, such as Stemline I™ and Stemline II™, Stem Span H3000® and or StemSpan SFEM® medium.

In a further preferred embodiment a medium for expansion according to the invention comprises thrombopoietin, flt-3 ligand, stem cell factor, IL-7, in conventional amounts as well as G-CSF, GM-CSF, IL-6, MIP-I-α, LIF, preferably in the amounts given in the examples.

In another embodiment the invention provides a differentiation and additionally an expansion+differentiation medium for simultaneously expansion/differentiation of stem cells into Natural Killer cell progenitors and subsequent maturation into functional mature NK-cells. The basic medium can be commercially available media such as Stemline I™ and Stemline II™, X-Vivo10™, X-Vivo15™, X-Vivo20™, StemSpan H3000®, StemSpan SFEM® medium, IMDM, DMEM, RPMI, HAMS F-10, HAMS F-12 etc. preferred is a mixture of 2:1 (v/v) DMEM and HAMs F-12. Human AB-serum has to be added in a final concentration between 1-25% preferably the amount of serum is around 5-15%.

A preferred combination of cytokines for expansion+differentiation medium is TPO, FLT-3L, SCF, IL-7, IL-2, IL-15, in conventional amounts and in addition GM-CSF, G-CSF, LIF, MIP-I-α and IL-6 preferably in the amounts given in the example. This medium is preferably applied after the initial expansion step of stem cells (5-15 days after initiation).

In a particularly preferred embodiment a method for expansion and differentiation comprises at least one change of conditions between an initial expansion medium and at least one subsequently applied expansion+differentiation medium as illustrated in FIG. 1:

Preferably the culture is initiated in serum-free conditions supplemented with lithium salt and 1-100 mg/l desulfated and/or further chemically modified UFH or LMWH. At some stage (preferably after 5-15 days of culture), preferably between day 7-11, the medium is exchanged with expansion+differentiation medium that preferably now contains human serum (1-25%, preferrably 10-20%) and IL-2. At some stage (preferably between day 10-23, preferably between day 13-20) the UFH/LMWH as well as the lithium salt that has been supplemented according to the invention is removed from the medium. This is preferably achieved by replacing the culture medium with fresh medium that does not contain said lithium. Typically this is achieved by replacing the culture medium with expansion and differentiation medium. In addition, at some stage (preferably between day 10-23, preferrably between day 11-15) the amount of the 3 cytokines flt3-L, SCF and TPO is reduced to amounts <4 ng/ml.

All media are preferably refreshed every other day, preferably 3 times/week. Refreshment is preferably achieved by replacing at least 30% of the medium with fresh medium. Preferably at least 50% of the medium is replaced, more preferably at least 100% of the medium is replaced. Refreshment of medium can be combined with exchangement of medium for changing from expansion medium to expansion and differentiation medium. It is preferred to adjust the medium quantity such that the cells at the start of the (continued) culture have a density of between 100,000 to 1,000,000 cells per ml of medium. Preferably a density of between 100,000 and 500,000 cells per ml of medium.

The invention also encompasses methods for maintaining while proliferating stem cells with the generation and expansion of progenitor cells, in particular stem cells from umbilical cord blood, BM or mPB, comprising harvesting stem cells from cord blood, culturing said cells in a medium according to the invention and separating the expanded cells from said medium. The invention further comprises methods for differentiating stem cells into NK progenitor cells and furthermore into functional mature NK-cells comprising culturing said stem cells, in particular stem cells derived from umbilical cord blood, BM or mPB, in an expansion+differentiation medium according to the invention and preferably culturing said stem cells in an expansion medium and subsequently in an expansion+differentiation medium in a scheme as given in the detailed description below. Culturing is preferably done under conventional suitable conditions typically encompassing temperatures of around 37 degrees Celsius, 100% RH, 10% $O_2$ and 5-7% $CO_2$.

The invention also encompasses proliferated and maintained stem cells produced by a process according to the invention.

The invention also encompasses natural killer progenitor cells produced by a method according to the invention.

In a further embodiment the invention comprises a set of media (kit of parts) for proliferation and maintenance of stem cells, in particular derived from cord blood, BM, or mPB and generation of primitive NK progenitor cells with subsequent expansion and functional maturation into mature NK-cells, comprising an expansion medium according to the invention, an expansion+differentiation medium according to the invention and preferably an instruction leaflet for use of the media.

The NK progenitor cells can be differentiated into mature and functional NK cells recognizing a desired target by specific receptors on their surface known to the expert in the field (CD56, CD16, CD107a, NKG2A/CD94, NKG2D, NCR receptors, KIR-receptors, etc.). These mature and functional NK cells can be generated in vitro according to the invention. The generated NK-progenitor-cells can be injected into patients as cellular therapeutic followed by in vivo expansion and maturation within the patients body. Alternatively, mature and functional active NK-cells can be generated in vitro according to the invention and injected as mature and functionally active NK-cells. Both above mentioned applications (NK-IC-progenitor infusion as well as infusion of in vitro maturated NK-cells) can be used for treatment of any kind of human disease preferably all malignant diseases such as tumors, cancer, leukemias as well as all viral diseases, also in solid transplant rejection situations and autoimmune diseases and loss of pregnancy.

In further embodiment the in vitro generated NK-cells as well the in vivo expanded and maturated NK-cells demonstrate functional killing activity against commonly accepted and used targets, such as malignant tumors. In addition, the cytokine producing activity of normal NK-cells is proven within the generated mature NK-cells Methods for (expanding and) differentiating stem cells into NK progenitor cells and onward into NK cells are also part of the present invention.

The target specific NK cells produced by these methods are also part of the present invention. Pharmaceutical compositions comprising progenitor cells or mature NK cells produced according to the invention and further comprising usual constituents of such compositions are also part of the present invention. Doses for such pharmaceutical compositions are generally expressed in the number of viable cells present in such a composition. Said number should be between $1-10\times10^6$ NK-IC or $1-10\times10^7$ mature NK-cells per kg body weight of a subject to be treated.

DETAILED DESCRIPTION OF THE INVENTION

Figure 1:
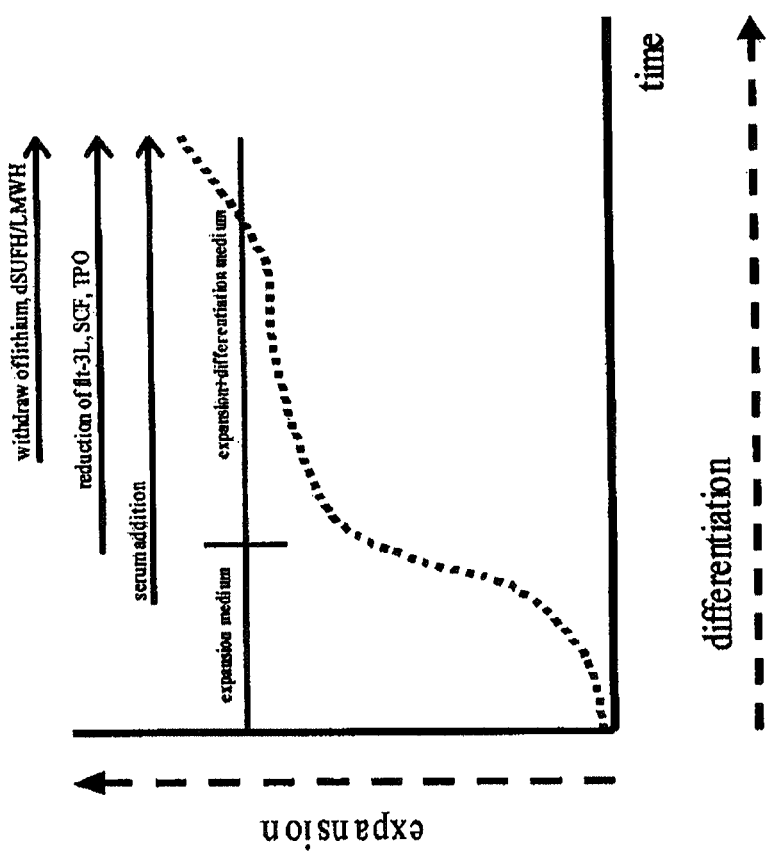
FIG. 1 is a graph schematically depicting that culturing cells in the medium of the present invention results both in expansion of cell number and in differentiation.

The following description discloses a method of in vitro generation of cellular therapeutics for clinical use that can be derived from small aliquots of postembryonic stem cells. This procedure is characterized by culturing postembryonic stem cells in a specifically formulated medium with a defined composition as well as a defined culture handling procedure to yield sufficient progenitors for clinical application.

The invention disclosed in here is at least in part based on the technical problem that for the treatment of malignant diseases, i.e. cancer, leukaemia and lymphoma as well as for transplant rejection situations and autoimmune diseases and loss of pregnancy. The availability of cellular therapies is very limited. With the exception of very few haematopoietic stem cell transplantations using umbilical cord blood (UCB), postembryonic stem cells have not been used for targeted cellular treatment in a non-allogeneic transplant setting without high dose chemotherapy/radiation-conditioning of the patient mainly due to the fact, that sufficient directed progenitor cells for cellular therapy are not available yet. In addition, these cells are alloreactive and cause severe graft-versus host disease in the recipient if treatment and cellular product are not optimal chosen.

The technical problem was at least partly solved in this invention by providing practicable procedures to generate sufficient numbers of progenitors as well as maturated effector cells for selected treatments as indicated herein before. The technical problem of selected progenitor generation of human postembryonic stem cells for clinical application could be solved by applying both well defined procedures of in vitro culture steps as well as specific changes of the culture conditions as described in the method section. These procedures allow for the first time the production of Natural-Killer-cell (NK-cell)-progenitors suitable in numbers and function for clinical application from small postembryonic stem cell aliquots.

The following postembryonic stem cells that can be obtained beginning from week 12 after gestation from foetal liver, perinatal umbilical cord blood (UCB), human bone marrow (BM) or G-CSF stimulated peripheral blood (mPB) can be isolated and used for cultivation procedures according to the invention. The person skilled in the art knows methods for the collection of these stem cells, whereby the harvest from perinatal umbilical cord, BM, or mPB is preferred for the procedures according to the invention.

In a further preferred embodiment of the procedures according to the invention a functional proof of the final cellular therapeutic is performed consecutive to cultivation. Especially preferred is the proof of progenitor features of Natural Killer Cells (NK-cells) as well as the proof function for active, mature NK-cells.

The Following Examples Illustrate the Invention:

1. Initiation of the In Vitro Culture and Expanding of Postembryonic Stem Cells:

Small aliquots of postembryonic stem cells (minimum 10-20 ml of human umbilical cord blood; an amount that is well below the required minimum amount for clinical banking) are processed according standard operating procedures of red cell lysis to obtain nucleated cells for further processing. As an option cells can be further purified by immunomagnetic cell separation according to the manufacturer (Miltenyi-Biotec, Germany) into enriched CD34+ cells (or alternatively CD133+ cells) and additionally CD14+ cells can be separated as well. The person of skill in this field will be able to perform these cell separations according to the manufacturer procedures. These cells are put in culture flasks or Teflon bags containing an expansion medium according to the described invention will be in this case the so called Glycostem-Expansion medium1 (GEM1):

The expansion medium or GEM1 according to the invention in this example consists of X-vivo10™ (Cambrex Inc.) containing 5% human AB-serum (Cambrex Inc.), Low-molecular-weight-heparin (LMWH), that is derived from a porcine mucosa heparin by cleavage with nitrous acid, in a concentration of 50 mg/l. The following recombinant human cytokines if not specifically mentioned all cytokines have been provided by Stem Cell Technology Inc. or R&D Systems): thrombopoietin (TPO; 35 ng/ml); flt-3Ligand (FLT-3L; 35 ng/ml), stem cell factor (SCF; 35 ng/ml), interleukin-7 (IL-7; 35 ng/ml), granulocyte-macrophage-colony-stimulating factor (GM-CSF; 10 pg/ml), granulocyte-colony-stimulating factor (G-CSF; 250 pg/ml), Leukaemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin 100 U/ml (Invitrogen), 25 µM 2-beta-mercaptoethanol (Invitrogen) ascorbic acid (20 mg/ml, Sigma), selenite selenite (50 µmol, Sigma), ethanolamine (50 µmol Sigma); lithium chloride (100 µmol Fluka).

The initiation of culture can be performed in 3 alternative ways:
  a) inoculation of nucleated cells after red cell lysis in GEM1-medium
  b) inoculation of separated CD34+ cells (or alternatively CD133+ cells) in GEM1-medium
  c) inoculation of separated CD34+ cells (or alternatively CD133+ cells) together with separated CD14+ cells as supplement in GEM1-medium at a ratio of 1 cell CD34+ [or alternatively CD133+ cells]: 1cell CD14+)

The final ratio of medium to inoculated cells is $1 \times 10^6$ total cells per 1 ml of medium or $1 \times 10^5$ CD34+ (or alternatively CD133+ cells). The culture conditions will be refreshed by adding new medium every $2^{nd}$ day. The following procedure will be preferred:
  Day 0: $1 \times 10^5$ CD34-positive cells were seeded in 1 ml of medium
  Day 2: addition of 1 ml GEM1-medium per $1 \times 10^5$ total input cells
  Day 4: addition of 1 ml GEM1-medium per $1 \times 10^5$ total input cells
  Day 6: addition of 1 ml GEM1-medium per $1 \times 10^5$ total input cells
  Day 8: addition of 1 ml GEM1-medium per $1 \times 10^5$ total input cells Cells are cultivated in the aforementioned expansion-medium according to the described invention with ratios under appropriate conditions. Appropriate conditions exemplary with regard to adequate culture containers, temperature, relative humidity, $O_2$ and $CO_2$ content of the gas phase are known to the expert. Preferentially the cells are cultivated in the aforementioned medium under the following conditions: (a) 37° C., (b) 100% relative humidity, (c) 10% $O_2$ and (d) 5% $CO_2$.

2. Initiation of Differentiation and Generation of the expanded postembryonic stem cells into a Natural Killer cell product in vitro:

At day 7-11 of culture the first change of the basal culture conditions regarding medium supplementation is performed. At this point the cellular suspension culture is driven into NK-cell differentiation.

The entire product is further differentiated into NK-progenitors and further matured into NK-cells during the culture period.

The designated amounts of the initial cell culture product are supplemented with an expansion and differentiation medium according to this invention. In this example at day 9 after initiation of culture an expansion and differentiation medium according to this invention will be added, the so called Glycostem-NK-cell-Expansion and Differentiation-Medium1 (GNKED1)

The medium consists of DMEM/Ham's F12-Medium (Invitrogen Inc.) volume-ratio 2:1 (V/V) containing 20% human AB-serum (Cambrex Inc.), Low-molecular-weight-heparin (LMWH) until day 16-18, that is derived from a porcine mucosa heparin by cleavage with nitrous acid, in a concentration of 50 mg/l. The following recombinant human cytokines if not specifically mentioned all cytokines have been provided by Stem Cell Technology Inc. or R&D Systems):

thrombopoietin (TPO; 1 ng/ml); flt-3Ligand (FLT-3L; 1 ng/ml), stem cell factor (SCF; 1 ng/ml), interleukin-7 (IL-7; 25 ng/ml), interleukin-15 (IL-15; 25 ng/ml), interleukin-2 (Proleukin© [Chiron]; 1000 U/ml), granulocyte-macrophage-colony-stimulating factor (GM-CSF; 10 pg/ml), granulocyte-colony-stimulating factor (G-CSF; 250 pg/ml), Leukaemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin 100 U/ml (Invitrogen), 25 µM 2-beta-mercaptoethanol (Invitrogen) ascorbic acid (20 mg/ml, Sigma), selenium selenite (50 µmol, Sigma), ethanolamine (50 µmol Sigma).

The culture conditions will be refreshed two days weekly by adding new medium. The following procedure will be preferred:

Day 9: addition of 5 ml GNKED1-medium per $1\times10^5$ total input cells

Day 13: addition of 5 ml GNKED1-medium per $1\times10^5$ total input cells

Day 16: addition of 5 ml GNKED1-medium per $1\times10^5$ total input cells

Day 20: addition of 5 ml GNKED1-medium without heparin per $1\times10^5$ total input cells Day 23: addition of 5 ml GNKED1-medium without heparin per $1\times10^5$ total input cells Day 27: addition of 5 ml GNKED1-medium without heparin per $1\times10^5$ total input cells Day 30: addition of 5 ml GNKED1-medium without heparin per $1\times10^5$ total input cells Cells are cultivated in the aforementioned medium according to this invention and ratios under appropriate conditions. Appropriate conditions exemplary with regard to adequate culture containers, temperature, relative humidity, $O_2$ and $CO_2$ content of the gas phase are known to the expert. Preferentially the cells are cultivated in the aforementioned medium under the following conditions: (a) 37° C., (b) 100% relative humidity, (c) 10% $O_2$ and (d) 5% $CO_2$.

Immature NK-cell progenitors (NK-IC) can be harvested from the cultures between day 15-20 after initiation followed by 2 washing steps in PBS containing 1% human AB-serum are performed according to standard operating procedures known to the person skilled in the field. Afterwards cells are resuspended in physiological NaCl-solution (0.9%) for infusion into the patient. After infusion, the NK-cells specifically maturate within the patients' body (in vivo) and finally differentiate in vivo into fully functional Natural Killer cells that are able to kill specific tumour cell targets.

Alternatively, cells will be expanded and differentiated until day 26-30 to obtain functionally maturated NK-cells that have expanded/differentiated >$2\times10^4$ fold from the input numbers. All cells are harvested and 2 washing steps in PBS containing 1% human AB-serum are performed according to standard operating procedures known to the person skilled in the field. As one embodiment of the invention, the maturated NK-cells will be activated overnight prior to intravenous application to the patient by cultivation in X-vivo15 medium, supplemented with 10% human AB-serum and IL-2 (1000 U/ml), IL-15 (25 ng/ml) and IL-18 (25 ng/ml). The next day cells will be washed twice and resuspended in physiological NaCl-solution (0.9%) for infusion into the patient.

The so generated and activated Natural Killer cells are able to kill specific tumour cell targets. For this reason the patient is preferably treated immediately after infusion with subcutaneous IL-2 (Proleukin©) at a dose of up to $2\times10^6$ IU/kg body weight.

Figure 2:
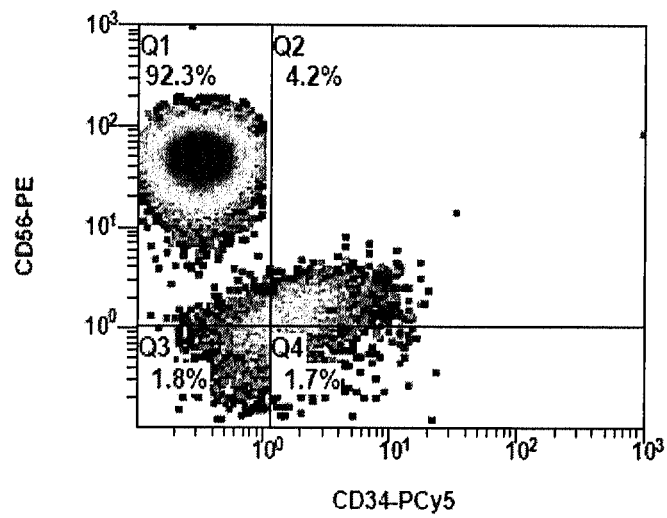
FIG. 2 is a plot graph showing an analysis of a small sample of generated NK-cells according to the present invention. This plot is gated on CD3-living cells and shows the correlation of CD56 and CD34 antigens.

A small aliquot of the cells is used for quality assurance control of the product and will be analysed phenotypically for mature and functional NK-cell in flowcytometry analyses.
Results of Experimental Example 1:

In 3 independent experiments (UCB-samples, amount between 10-25 ml) CD34+-cells were enriched and $1\times10^3$ cells were expanded in GEM1 medium according to the invention for 9 days followed by an 18 day expansion and differentiation in GNKED1 medium. The total amount of $CD56^+/CD3^-$ cells generated in these experiments was $2.05\pm0.35\times10^7$ cells with an amount of 90.5±4.2% living cells and a purity of 92.0±5.1% total NK-cells (FIG. 2). In the control experiment without the inventive steps $0.67\pm0.33\times10^6$ NK-cells were generated with mean survival of 46±4.1% and a purity of 34.1±6.6% (FIG. 3).

FIG. 2: The Plot shows an analysis of a small sample of generated NK-cells according to the described invention. This plot is gated on CD3− living cells and shows the correlation of CD56 and CD34 antigens.

The generated cells in this example contain more than 92% CD56+/CD3− NK-cells.

Figure 3:
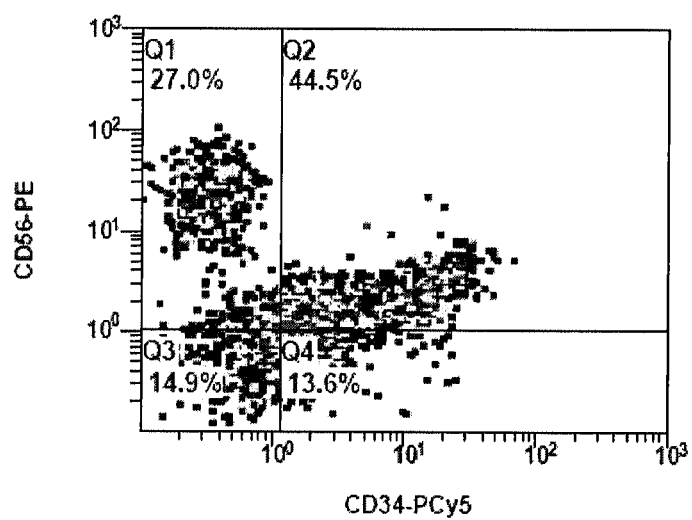
FIG. 3 is a plot graph showing an analysis of a small sample of generated NK-cells not according to the present invention. This plot is gated on CD3-living cells and shows the correlation of CD56 and CD34 antigens.

FIG. 3: The Plot shows an analysis of a small sample of generated NK-cells without inventive steps. This plot is gated on CD3− living cells and shows the correlation of CD56 and CD34 antigens.

Experimental Example 2

In a second setup of experiments small aliquots of postembryonic stem cells (minimum 10-20 ml of human umbilical cord blood or BM) are processed according standard operating procedures of red cell lysis to obtain nucleated cells for further processing. As an option cells can be further purified by immunomagnetic cell separation according to the manufacturer (Miltenyi-Biotec, Germany) into enriched CD34+ cells (or alternatively CD133+ cells) and additionally CD14+ cells can be separated as well. The person of skill in this field will be able to perform these cell separations according to the manufacturer procedures. These cells are put in culture flasks or Teflon bags containing an expansion medium according to the described invention will be in this case the so called Glycostem-Expansion medium2 (GEM2):

The medium according to the described invention in this example consists of StemSpan H3000® (Stem Cell Technology Inc.) containing no serum but completely desulfated heparin (Seikagaku), of 20 mg/l. The following recombinant human cytokines if not specifically mentioned all cytokines have been provided by Stem Cell Technology Inc. or R&D Systems): Interleukin-3 (IL-3; 5 ng/ml) thrombopoietin (TPO; 25 ng/ml); flt-3Ligand (FLT-3L; 25 ng/ml), stem cell factor (SCF; 25 ng/ml), interleukin-7 (IL-7; 25 ng/ml), granulocyte-macrophage-colony-stimulating factor (GM-CSF; 10 pg/ml), granulocyte-colony-stimulating factor (G-CSF; 250 pg/ml), Leukaemia-inhibitory factor (LIF; 50 pg/ml), Macrophage-inflammatory protein-1alpha (200 pg/ml; MIP-I alpha) and interleukin-6 (IL-6; 50 pg/ml). Additional, supplements are L-glutamine (2 mmol/l; Invitrogen), penicillin (1000 U/ml), streptomycin 100 U/ml (Invitrogen), 25 µM 2-beta-mercaptoethanol (Invitrogen) ascorbic acid (20 mg/ml, Sigma), selenium selenite (50 µmol, Sigma), ethanolamine (50 µmol Sigma).

The initiation of culture can be performed in 3 alternative ways:

d) inoculation of nucleated cells after red cell lysis in GEM2-medium e) inoculation of separated CD34+ cells (or alternatively CD133+ cells) in GEM2-medium f) inoculation of separated CD34+ cells (or alternatively CD133+ cells) together with separated. CD14+ cells as supplement in GEM2-medium at a ratio of 1 cell CD34+ [or alternatively CD133+ cells]: 1cell CD14+)

The final ratio of medium to inoculated cells is $1 \times 10^6$ total cells per 1 ml of medium or $1 \times 10^5$ CD34+ (or alternatively CD133+ cells). The culture conditions will be refreshed by adding new medium every $2^{nd}$ day. The following procedure will be preferred:

Day 0: $1 \times 10^5$ CD34-positive cells were seeded in 1 ml of medium

Day 2: addition of 1 ml GEM2-medium per $1 \times 10^5$ total input cells

Day 4: addition of 1 ml GEM2-medium per $1 \times 10^5$ total input cells

Day 6: addition of 1 ml GEM2-medium per $1 \times 10^5$ total input cells

Day 8: addition of 1 ml GEM2-medium per $1 \times 10^5$ total input cells

Cells are cultivated in the aforementioned medium according to the described invention and ratios under appropriate conditions. Appropriate conditions exemplary with regard to adequate culture containers, temperature, relative humidity, $O_2$ and $CO_2$ content of the gas phase are known to the expert.

Preferentially the cells are cultivated in the aforementioned medium under the following conditions: (a) 37° C., (b) 100% relative humidity, (c) 10% $O_2$ and (d) 5% $CO_2$.

2. Initiation of Differentiation and Generation of the Expanded Postembryonic Stem Cells into a Natural Killer Cell Product In Vitro:

At day 7-11 of culture in the first change in the basal culture conditions regarding medium supplementation is performed. At this point the cellular suspension culture is driven into NK-cell differentiation.

The entire product is further differentiated into NK-progenitors and further matured into NK-cells during the culture period.

The designated amounts of the initial cell culture product are supplemented with an expansion+differentiation medium according to the described invention. In this example at day 9 after initiation of culture a medium according to the described invention will be added the so called Glycostem-NK-cell-Expansion and Differentiation-Medium2 (GNKED2):

The medium according to the described invention consists of DMEM/Ham's F12-Medium (Invitrogen Inc.) volume-ratio 2:1 (V/V) containing 10% human AB-serum (Cambrex Inc.), completely desulfated heparin (Seikagaku), of 20 mg/l until day 16-18. The following recombinant human cytokines (if not specifically mentioned all cytokines have been provided by Stem Cell Technology Inc. or R&D Systems): thrombopoietin (TPO; 1 ng/ml); flt-3Ligand (FLT-3L; 1 ng/ml), stem cell factor (SCF; 1 ng/ml), interleukin-7 (IL-7; 25 ng/ml), interleukin-15 (IL-15; 25 ng/ml), interleukin-2 (Proleukin© [Chiron]; 1000 U/ml), granulocyte-macrophage-colony-stimulating factor (GM-CSF; 10 pg/ml), granulocyte-colony-stimulating factor (G-CSF; 250 pg/ml), Leukaemia-inhibitory factor (LIF; 50 pg/ml), Macrophage-inflammatory protein-1alpha (200 pg/ml; MIP-I alpha) and interleukin-6 (IL-6; 50 pg/ml). Additional supplements are L-glutamine (2 mmol/l; Invitrogen), penicillin (1000 U/ml), streptomycin 100 U/ml (Invitrogen), 25 µM 2-beta-mercaptoethanol (Invitrogen) ascorbic acid (20 mg/ml, Sigma), selenium selenite (50 µmol, Sigma), ethanolamine (50 µmol Sigma).

The culture conditions will be refreshed two days weekly by adding new medium. The following procedure will be preferred:

Day 9: addition of 5 ml GNKED2-medium per $1 \times 10^5$ total input cells

Day 13: addition of 5 ml GNKED2-medium per $1 \times 10^5$ total input cells

Day 16: addition of 5 ml GNKED2-medium per $1 \times 10^5$ total input cells

Day 20: addition of 5 ml GNKED2-medium without heparin per $1 \times 10^5$ total input cells Day 23: addition of 5 ml GNKED2-medium without heparin per $1 \times 10^5$ total input cells Day 27: addition of 5 ml GNKED2-medium without heparin per $1 \times 10^5$ total input cells Day 30: addition of 5 ml GNKED2-medium without heparin per $1 \times 10^5$ total input cells Cells are cultivated in the aforementioned medium according to the described invention and ratios under appropriate conditions. Appropriate conditions exemplary with regard to adequate culture containers, temperature, relative humidity, $O_2$ and $CO_2$ content of the gas phase are known to the expert. Preferentially the cells are cultivated in the aforementioned medium under the following conditions: (a) 37° C., (b) 100% relative humidity, (c) 10% $O_2$ and (d) 5% $CO_2$.

Immature NK-cell progenitors (NK-IC) can be harvested from the cultures between day 15-20 after initiation followed by 2 washing steps in PBS containing 1% human AB-serum are performed according to standard operating procedures known to the person skilled in the field. Afterwards cells are resuspended in physiological NaCl-solution (0.9%) for infusion into the patient. After infusion, the NK-cells specifically maturate within the patients' body (in vivo) and finally differentiate in vivo into fully functional Natural Killer cells that are able to kill specific tumour cell targets.

Alternatively, cells will be expanded and differentiated until day 26-30 to obtain functionally maturated NK-cells that have expanded/differentiated $>2 \times 10^4$ fold from the input numbers. All cells are harvested and 2 washing steps in PBS containing 1% human AB-serum are performed according to standard operating procedures known to the person skilled in the field. As one embodiment of the invention, the maturated NK-cells will be activated overnight prior to intravenous application to the patient by cultivation in x-vivo-15 medium; supplemented with 10% human AB-serum and IL-2 (1000 U/ml), IL-15 (25 ng/ml) and IL-18 (25 ng/ml). The next day cells will be washed twice and resuspended in physiological NaCl-solution (0.9%) for infusion into the patient.

The so generated and activated Natural Killer cells are able to kill specific tumour cell targets. For this reason the patient is preferably treated immediately after infusion with subcutaneous IL-2 (Proleukin©) at a dose of $2 \times 10^6$ IU/kg body weight.

A small aliquot of the cells is used for quality assurance control of the product and will be analysed phenotypically for mature and functional NK-cell in flowcytometry analyses.

Figure 4:
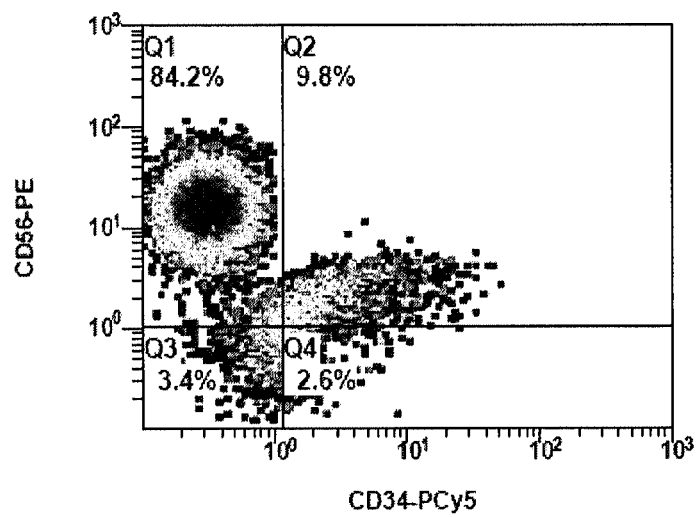
FIG. 4 is a plot graph showing an analysis of a small sample of generated NK-cells according to the present invention. This plot is gated on CD3-living cells and shows the correlation of CD56 and CD34 antigens.

Results of Experimental Example 2:

In 3 independent UCB-samples (amount between 10-25 ml) CD34+ cells were enriched and $1 \times 10^3$ cells were expanded in GEM2 medium according to the described invention for 9 days followed by an 18 day expansion and differentiation in GNKD2 medium. The total amount of CD56+/CD3− cells in these experiments was $2.13 \pm 0.55 \times 10^7$ cells with an amount of 86.2±5.6% living cells and an purity of 83.8±4.8% total NK-cells (FIG. 4). In the control experiments without crucial inventive steps $0.97 \pm 0.13 \times 10^6$ NK-cells were generated with a mean survival of 55.3±7.2% and a purity of 44±5.6% (FIG. 5)

FIG. 4: The Plot shows an analysis of a small sample of generated NK-cells according to the described invention. This plot is gated on CD3− living cells and shows the correlation of CD56 and CD34 antigens.

The medium used in this cultivation period according to the described invention contains heparin as mentioned above. The generated NK-cell Population CD56+/CD3− cells in this example contain more than 84% NK-cells.

Figure 5:
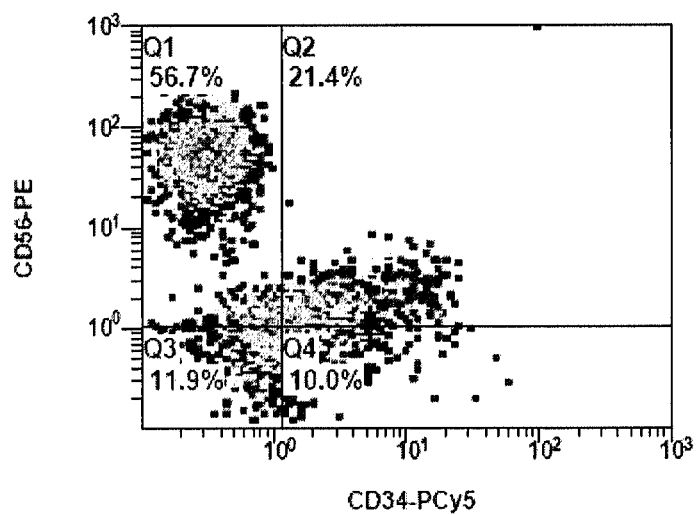
FIG. 5 is a plot graph showing an analysis of a small sample of generated NK-cells according to the present invention. This plot is gated on CD3-living cells and shows the correlation of CD56 and CD34 antigens.

FIG. 5: The Plot shows an analysis of a small sample of generated NK-cells according to the described invention. This plot is gated on CD3− living cells and shows the correlation of CD56 and CD34 antigens.

The invention claimed is:

1. A method for-generating a collection of differentiated cells comprising culturing cells from a sample comprising stem cells, progenitor cells or both, from human postembryonic tissue in an expansion medium comprising desulphated glycosaminoglycan (GAG), three or more of TPO, FLT-3L, SCF, IL-7, IL-3, IL-15, and in addition three or more of GM-CSF, G-CSF, LIF, MIP-1-α and IL 6 followed by culturing the cells in an expansion and differentiation medium comprising a collection of cytokines, desulphated glycosaminoglycan (GAG) and human serum, wherein said collection of cytokines comprises three or more of TPO, FLT-3L, SCF, IL-7, IL-2, IL-15, and in addition three or more of GM-CSF, G-CSF, LIF, MIP-1-α and IL-6, wherein the cultured isolated cells are expanded and differentiated to generate the collection of differentiated cells.

2. A method according to claim 1, wherein said expansion medium further comprises lithium.

3. A method according to claim 1, wherein the expansion medium is switched to expansion and differentiation medium by stepwise replacement and/or dilution of expansion culture medium with expansion and differentiation medium.

4. A method according to claim 1, wherein the concentration of FLT-3, TPO and/or SCF is reduced during culture in the expansion and differentiation medium.

5. A method according to claim 1, wherein lithium and/or desulphated glycosaminoglycan is reduced during culture in the expansion and differentiation medium.

6. A method according to claim 1, wherein said desulphated glycosaminoglycan comprises heparin.

7. A method according to claim 1, wherein said desulphated glycosaminoglycan comprises low molecular weight heparin.

8. A method according to claim 1, further comprising collecting culture cells.

9. A kit of parts for generating natural killer cells from progenitor cells, stem cells or both said kit comprising an expansion and differentiation medium comprising a collection of cytokines, desulphated glycosaminoglycan (GAG) and human serum, wherein said collection of cytokines comprises three or more of TPO, FLT-3L, SCF, IL-7, IL-2, IL-15, and in addition GM-CSF, G-CSF, LIF, MIP-1-α and IL-6, and/or the components thereof in amounts sufficient for producing said medium.

10. A kit of parts according to claim 9, further comprising an expansion medium comprising a collection of cytokines and desulphated glycosaminoglycan (GAG), wherein said collection of cytokines comprises three or more of TPO, FLT-3L, SCF, IL-7, IL-3, IL-15, and in addition GM-CSF, G-CSF, LIF, MIP-1-α and IL-6, and/or the components thereof in amounts sufficient for producing said medium.

11. A method according to claim 1, further comprising collecting cultured cells and administering said cells to an individual.

12. A method according to claim 1, further comprising treatment of an individual suffering from a tumor, a viral infection or both, said treatment comprising administering to said individual cultured cells from said culture.

13. A method according to claim 1, further comprising treatment of an individual suffering from an autoimmune disease, transplant rejection or loss of pregnancy, said treatment comprising administering to said individual cultured cells from said culture.

14. A method for generating a collection of differentiated natural killer cells comprising culturing somatic stem cells from a sample from human postembryonic tissue in an expansion medium comprising three or more of TPO, FLT-3L, SCF, IL-7, IL-3, IL-15, and in addition three or more of GM-CSF, G-CSF, LIF, MIP-1-α and IL-6, and desulphated glycosaminoglycan (GAG) and after about 5 to 15 days of culturing in the expansion medium the expansion medium is replaced by an expansion and differentiation medium comprising a collection of cytokines, desulphated glycosaminoglycan (GAG) and human serum, wherein said collection of cytokines comprises three or more of TPO, FLT-3L, SCF, IL-7, IL-2, IL-15, and in addition three or more of GM-CSF, G-CSF, LIF, MIP-1-α and IL-6, in which expansion and differentiation medium the cells are further cultured and wherein the cultured cells are expanded and differentiated to generate the collection of differentiated natural killer cells.

* * * * *